United States Patent
Bettarini et al.

(10) Patent No.: US 6,632,775 B1
(45) Date of Patent: **\*Oct. 14, 2003**

(54) HERBICIDAL COMPOSITIONS

(75) Inventors: Franco Bettarini, Novara (IT); Ernesto Signorini, Malnate Varese (IT); Piero La Porta, deceased, late of Novara (IT), by Paola Sapino, heiress; Sergio Massimini, Milan (IT); Domenico Portoso, Lodi (IT)

(73) Assignee: Isagro Ricerca S.r.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,984
(22) PCT Filed: Jun. 2, 1998
(86) PCT No.: PCT/EP98/03472
§ 371 (c)(1), (2), (4) Date: Dec. 3, 1999
(87) PCT Pub. No.: WO98/54967
PCT Pub. Date: Dec. 10, 1998

(30) Foreign Application Priority Data

Jun. 5, 1997 (IT) .......................... MI97A1325

(51) Int. Cl.⁷ ...................... A01N 43/824; A01N 43/84; C07D 285/12
(52) U.S. Cl. .................. 504/139; 504/105; 504/116; 504/225; 504/263; 548/136
(58) Field of Search ............... 504/139, 263, 504/225; 548/136

(56) References Cited

U.S. PATENT DOCUMENTS 3,746,719 A  *  7/1973  Sasse et al. ............... 260/306.8
4,067,720 A  *  1/1978  Perronnet et al. ............... 71/90
5,821,197 A  * 10/1998  Battarini et al. ............ 504/263

FOREIGN PATENT DOCUMENTS

GB       1232349       *  5/1971

* cited by examiner

*Primary Examiner*—Sabiha Qazi
(74) *Attorney, Agent, or Firm*—Oblon, Spivak, McClelland, Maier & Neustadt, P.C.

(57) ABSTRACT

A herbicidal composition, comprising:
(a) at least one arylthiadiazole having the formula (I):

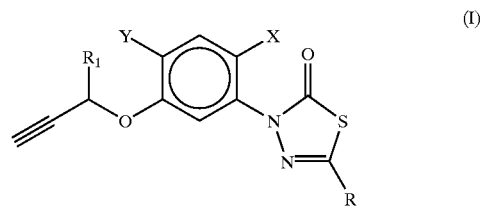

wherein:
R represents linear or branched $C_1$–$C_6$ alkyl or haloalkyl; or $C_3$–$C_5$ cycloalkyl or halocycloalkyl; said alkyl, haloalkyl, cycloalkyl or halocycloalkyl being optionally substituted with linear or branched $C_1$–$C_3$ alkyl;
X represents halogen;
Y represents halogen; linear or branched $C_1$–$C_4$ alkyl or haloalkyl; linear or branched $C_1$–$C_4$ alkoxyl or haloalkoxyl;
$R_1$ represents hydrogen or methyl; and
(b) one or more herbicidal compounds.

12 Claims, No Drawings

HERBICIDAL COMPOSITIONS

BACKGROUND OF THE INVENTION

Field of the Invention

The present invention relates to herbicidal compositions.

SUMMARY OF THE INVENTION

More specifically, the present invention relates to herbicidal compositions comprising at least one arylthiadiazolone and one or more known herbicides and their use as herbicides for controlling weeds in agricultural crops.

DETAILED DESCRIPTION OF THE PREFERRED EMBODIMENTS

The Applicant has in fact found that herbicidal compositions containing one or more known herbicides and at least one compound belonging to the group of 3-aryl-1,3,4-thiadiazol-2(3H)-ones, have a surprisingly high herbicidal activity towards numerous weeds but, at the same time, are not phytotoxic with respect to important agricultural crops.

The present invention therefore relates to herbicidal compositions comprising:

(a) at least one arylthiadiazolone having general formula (I):

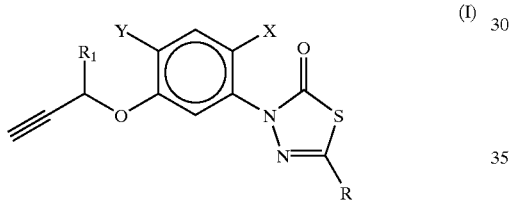

wherein:
R represents a linear or branched $C_1$–$C_6$ alkyl or haloalkyl group; or a $C_3$–$C_6$ cycloalkyl or halocycloalkyl group; said alkyl or haloalkyl, cycloalkyl or halocycloalkyl groups, optionally substituted with linear or branched $C_1$–$C_3$ alkyl groups;

X represents a halogen atom such as chlorine or fluorine;

Y represents a halogen atom such as chlorine, fluorine, bromine or iodine; a linear or branched $C_1$–$C_4$ alkyl or haloalkyl group; a linear or branched $C_1$–$C_4$ alkoxyl or haloalkoxyl group;

$R_1$ represents a hydrogen atom or a methyl group;

(b) one or more herbicides selected from the following: chloramben, chlorthal, dicamba, naptalam, 2,3,6-TBA, clopyralid, diflufenzopyr (SAN 835 H), dithiopyr, picloram, thiazopyr (MON 13200), quinclorac, quinmerac, indanofan (MK-243), benazolin, chlorflurenol, dalapon, endothal, flamprop, flamprop M, flupropanate, flurenol, TCA-sodium, bromobutide, chlorthiamid, diflufenican, diphenamid, ethabenzanid (HW 52), isoxaben, mefenacet, monalide, pentanochlor, propanil, propyzamide, tebutam, fluthiamide (BAY FOE 5043), clodinafop, clomeprop, cyhalofop-butyl (XDE-537), 2,4-D, 2,4-DB, dichlorprop, dichlorprop-P, diclofop, fenoxaprop, fenoxaprop-P, fluazifop, fluazifop-P, fluroxypyr, haloxyfop, haloxyfop-P-methyl, isoxapyrifop, MCPA, MCPA-thioethyl, MCPB, mecoprop, mecoprop-P, naproanilide, napropamide, propaquizafop, quizalofop, quizalofop-P, triclopyr, UBI-C4874, bromofenoxim, bromoxynil, dichlobenil, ioxynil, diquat, paraquat, asulam, butylate, carbetamide, chlorbufam, chlorpropham, cycloate, desmedipham, dimepiperate, EPTC, esprocarb, molinate, orbencarb, pebulate, phenmedipham, propham, prosulfocarb, pyributicarb, thiobencarb, tiocarbazil, tri-allate, vernolate, alloxydim, butroxydim, clethodim, cycloxydim, sethoxydim, sulcotrione, tralkoxydim, acetochlor, alachlor, butachlor, butenachlor, diethatyl, dimethachlor, dimethenamid, metazachlor, metolachlor, pretilachlor, propachlor, propisochlor, tenylchlor (NSK-850), acifluorfen, aclonifen, bifenox, chlomethoxyfen, chlornitrofen, athoxyfen-ethyl (HC-252), fluoroglycofen, fluoronitrofen, fomesafen, furyloxyfen, lactofen, AKH-7088, oxyfluorfen, benfluralin, butralin, dinitramide, ethalfluralin, fluchloralin, isopropalin, oryzalin, pendimethalin, prodiamine, trifluralin, dinoseb, dinoseb acetate, dinoterb, amitrole, benfuresate, bentazone, benzofenap, cafenstrole (CH-900), carfentrazone-ethyl (F-8426), chloridazon, cinmethylin, clomazone, difenzoquat, ethofumesate, pyraflufen-ethyl (ET-751), flumiclorac-pentyl, flumioxazin, flumipropin, flupoxam, fluridone, flurochloridone, flurtamone, fluthiacet methyl (KIH-9201), isoxaflutone (RPA 201772), methazole, nipyraclofen, norflurazon, oxadiargyl, oxadiazon, oxaziclomefone (MY-100), pentoxazone (KPP-314), pyrazolynate, pyrazoxyfen, pyridate, sulfentrazone (F6285), thidiazimin, anilofos, bensulide, bilanafos, butamifos, fosamine, glufosinate, glyphosate, LS830556, piperophos, imazamethabenz, imazamethipyr (AC-263,222), imazamox (AC-299,263), imazapyr, imazaquin, imazethapyr, bispyribac-sodium (KHI-2023), pyribenzoxim (LGC-40863), pyriminobac-methyl (KIH-6127), pyrithiobac-sodium (KIH-2031), tioclorim, cloransulam-methyl (XDE-565), diclosulam (XDE-564), flumetsulam (DE-498), metosulam (DE-511), amidosulfuron, azimsulfuron (DPX-A8947), bensulfuron, chlorimuron, chlorsulfuron, cinosulfuron, cyclosulfamuron (AC-322,140), etha-metsulfuron-methyl (DPX-A7881), ethoxysulfuron (HOE 095404), flazasulfuron, flupyrsulfuron (DPX-KE459), halosulfuron (NC-319), imazosulfuron, metsulfuron, NC-330, nicosulfuron, oxasulfuron (CGA-277476), primisulfuron, prosulfuron (CGA-152005), pyrazosulfuron, rimsulfuron, sulfometuron (DPX-5648), sulfosulfuron (MON-37500), thifensulfuron, triasulfuron (CGA-131036), tribenuron, triflusulfuron-methyl (DPX-66037), ametryn, atrazine, aziprotryne, cyanazine, desmetryn, dimethame-tryn, dipropetryn, eglinazine, methoprotryne, proglinazine, prometon, prometryne, propazine, simazine, simetryn, terbumeton, terbuthylazine, terbutryn, triaziflam (IDH-1105), trietazine, SMY-1500, hexazinone, metamitron, metribuzin, bromacil, lenacil, terbacil, benzthiazuron, chlorbromuron, chloroxuron, chlorotoluron, cumyluron (JC-940), daimuron, difenoxuron, dimefuron, 1-diuron, ethidimuron, fenuron, fluometuron, isoproturon, isouron, linuron, methabenzthiazuron, methyldymron, metobenzuron, metobromuron, metoxuron, monolinuron, neburon, siduron, tebuthiuron, thiazafluron, isopropazol (JV 485), KPP 300, KPP 421, BAY YRL 2388, DPXT 5975, azafenidin.

Specific examples of arylthiadiazolones having general formula (I) which can be used for the purposes of the present invention are:

3-[2,4-dichloro-5-(2-propinyloxy)phenyl]-5-(1,1-dimethylethyl)-1,3,4-thiadiazol-2(3H)-one (Compound Nr. 1);

3-[4-chloro-2-fluoro-5-(2-propinyloxy)phenyl]-5-(1,1-dimethylethyl)-1,3,4-thiadiazol-2(3H)-one (Compound Nr. 2);

5-cyclopropyl-3-[2,4-dichloro-5-(2-propinyloxy)phenyl]-1,3,4-thiadiazol-2(3H)-one (Compound Nr. 3);

5-cyclopropyl-3-[4-chloro-2-fluoro-5-(2-propinyloxy)phenyl]-1,3,4-thiadiazol-2(3H)-one (Compound Nr. 4);

3-[2,4-dichloro-5-(2-propinyloxy)phenyl]-5-(1-methylethyl)-1,3,4-thiadiazol-2(3H)-one (Compound Nr. 5);

3-[4-chloro-2-fluoro-5-(2-propinyloxy)phenyl]-5-(1-methylethyl)-1,3,4-thiadiazol-2(3H)-one (Compound Nr. 6);

3-[2,4-dichloro-5-(2-propinyloxy)phenyl]-5-ethyl-1,3,4-thiadiazol-2(3H)-one (Compound Nr. 7);

3-[4-chloro-2-fluoro-5-(2-propinyloxy)phenyl]-5-ethyl-1,3,4-thiadiazol-2(3H)-one (Compound Nr. 8)

3-[2,4-dichloro-5-(2-propinyloxy)phenyl]-5-(1-methylcyclopropyl)-1,3,4-thiadiazol-2(3H)-one (Compound Nr. 9);

3-[4-chloro-2-fluoro-5-(2-propinyloxy)phenyl]-5-(1-methylcyclopropyl)-1,3,4-thiadiazol-2(3H)-one (Compound Nr. 10);

(±)-3-[2,4-dichlorophenyl-5-(1-methyl-2-propinyloxy)phenyl]-5-(1,1-dimethylethyl)-1,3,4-thiadiazol-2(3H)-one (Compound Nr. 11);

(±)-3-[4-chloro-2-fluoro-5-(1-methyl-2-propinyloxy)phenyl]-5-(1,1-dimethylethyl)-1,3,4-thiadiazol-2(3H)-one (Compound Nr. 12);

(±)-5-cyclopropyl-3-[2,4-dichloro-5-(1-methyl-2-propinyloxy)phenyl]-1,3,4-thiadiazol-2(3H)-one (Compound Nr. 13);

(±)-5-cyclopropyl-3-[4-chloro-2-fluoro-5-(1-methyl-2-propinyloxy)phenyl]-1,3,4-thiadiazol-2(3H)-one (Compound Nr. 14);

(±)-3-[2,4-dichloro-5-(1-methyl-2-propinyloxy)phenyl]-5-(1-methylethyl)-1,3,4-thiadiazol-2(3H)-one (Compound Nr. 15);

(±)-3-[4-chloro-2-fluoro-5-(1-methyl-2-propinyloxy)phenyl]-5-(1-methylethyl)-1,3,4-thiadiazol-2(3H)-one (Compound Nr. 16);

(±)-3-[2,4-dichloro-5-(1-methyl-2-propinyloxy)phenyl]-5-ethyl-1,3,4-thiadiazol-2(3H)-one (Compound Nr. 17)

(±)-3-[4-chloro-2-fluoro-5-(1-methyl-2-propinyloxy)phenyl]-5-ethyl-1,3,4-thiadiazol-2(3H)-one (Compound Nr. 18);

(±)-3-[2,4-dichloro-5-(1-methyl-2-propinyloxy)phenyl]-5-(1-methylcyclopropyl)-1,3,4-thiadiazol-2(3H)-one (Compound Nr. 19);

(±)-3-[4-chloro-2-fluoro-D-(1-methyl-2-propinyloxy)phenyl]-5-(1-methylcyclopropyl)-1,3,4-thiadiazol-2(3H)-one (Compound Nr. 20).

The arylthiadiazolones having general formula (I) can be conveniently prepared by means of various processes.

One process for the preparation of the arylthiadiazolones having general formula (I) comprises the reaction of a thiohydrazide having general formula (II):

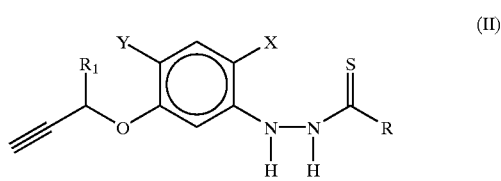

(II)

wherein X, Y, R and $R_1$ have the same meanings described above, with phosgene, trichloromethylchloroformiate or bis(trichloromethyl)carbonate, in the presence of or without, preferably in the presence of, an inert organic solvent, at a temperature ranging from +20° C. to the boiling point of the mixture itself, optionally in the presence of an organic or inorganic base.

Inert organic solvents which can be used for the purpose are chlorinated hydrocarbons such as, for example, methylene chloride, chloroform, 1,2-dichloroethane, etc; aromatic hydrocarbons such as, for example, benzene, toluene, xylene, chlorobenzene, etc; ethers such as, for example, ethyl ether, tetrahydrofuran, dimethoxyethane, dioxane, etc; esters such as, for example, ethyl acetate, etc.

Organic bases which can be used for the purpose are, for example, triethylamine, pyridine, 4-dimethylaminopyridine, etc.

Inorganic bases which can be used for the purpose are, for example, sodium bicarbonate, etc.

The thiohydrazides having general formula (II) can be prepared by treatment of the corresponding hydrazides with phosphorous pentasulfide or with the Lawesson reagent as described, for example, in "Journal of Fluorine Chemistry" (1978), Vol. 2, pages 1–21, or in "Chemistry Express" (1991), Vol. 6, pages 411–414.

The herbicides (b) are all products which are known in the art and commercially available. The herbicides (b) listed above, are indicated with their common name or with their code number as specificed, for example, in "The Agrochemicals Handbook (1994)", Third Edition, Royal Society of Chemistry; or in "AG Chem New Compound Review", Vol. 13 (1995), Vol. 14 (1996) and Vol. 15 (1997), W. L. Hopkins, AG Chem Information Service; or in "Brighton Crop Protection Conference-Proceedings", (1991), (1993) and (1995).

The use of the herbicidal compositions of the present invention has proved to be advantageous with respect to the use of the known herbicides (b) listed above, on their own, in that the presence of at least one arylthiadiazolone having general formula (I) allows the use of reduced doses of these herbicides which are often phytotoxic, and/or enlarge the action spectrum.

The herbicidal compositions of the present invention have proved to be particularly effective in both pre-emergence and post-emergence treatment, in the control of numerous weeds, both monocotyledons and dicotyledons. At the same time, these herbicidal compositions have shown a reduced or no phytotoxicity towards important agricultural crops, therefore making it possible for them to be used in the agrarian field in the selective control of weeds.

Examples of weeds which can be effectively controlled with the herbicidal compositions of the present invention are: *Abutilon theofrasti, Alisma plantago, Alopecurus myosuroides*, Amaranthus spp., *Ambrosia artemisifolia,* Amnimaius, *Apera spica venti, Avena fatua*, Bromus spp., *Capsella bursa pastoris, Cassia obtusifolia, Chenopodium album, Convolvulus sepium,* Cyperus spp., *Datura stramonium, Digitaria sanguinalis,* Echinochloa spp., *Eleusine indica, Galium aperine, Geranium dissectum,*

*Heleocharis avicularis*, Heteranthera spp., Ipomea spp., Lolium spp., Matricaria spp., *Monochoria vaginalis*, Panicum spp., *Papaver rhoaes, Phaseolus aureus*, Poa spp., Polygonum spp., *Portulaca oleracea, Rotala indica, Sagittaria pigmaea*, Scirpus spp., *Sesbania exaltata, Setaria viridis, Sida spinosa*, Sorgum spp., *Solanum nigrum, Stellaria media*, Veronica spp., *Vicia fabae, Viola arvensis*, Xanthium spp., etc.

At the doses used for agrarian applications, the herbicidal compositions of the present invention have had no toxic effects with respect to one or more important agricultural crops such as, for example, maize (*Zea mais*), wheat (*Triticum* Spp.), soya (*Glicine max*), rice (*Oryza sativa*), etc.

The arylthiadiazolones having general formula (I) and the herbicides (b) listed above, forming the above herbicidal compositions, can be combined in any ratio, depending on various factors such as, for example, the number and type of constituents of the mixture, the crop to be protected, the weeds to be eliminated, the degree of infestation, the application method, the characteristics of the soil, etc.

In the herbicidal compositions of the present invention, the weight quantity of the arylthiadiazolone having general formula (I) can generally vary from 1 g/ha to 5 kg/ha, preferably from 10 g/ha to 500 g/ha.

In the herbicidal compositions of the present invention, the ratio between the weight quantity of the arylthiadiazolone having general formula (I) and the weight quantity of the product(s) with a herbicidal activity (b) listed above, can generally vary from 99.9:0.1 to 0.1:99.9, preferably from 99:1 to 1:99.

In the case of pre-emergence treatment in cultivations of maize, cereals or soya, the herbicidal compositions of the present invention comprise, in addition to the arylthiadiazolone having general formula (I), one or more of the following herbicides (b), to be selected from those listed above, on the basis of the crop in question and weeds to be eliminated: acetochlor, acifluorfen, aclonifen, alachlor, ametryn, atrazine, bifenox, butralin, chloramben, clomazone, chlorbromuron, chlorotoluron, chlorsulfuron, cyanazine, cyclosulfamuron (AC-322,140), diethatyl, diflufenican, dimethenamid, diphenamid, eglinazine, fluchloralin, flumioxazin, fluoroglycofen, flupoxam, flurochloridone, flurtamone, halosulfuron (NC-319), imazaquin, imazethapyr, isoproturon, isoxaben, isoxaflutole (RPA 201772), linuron, metazachlor, methabenzthiazuron, metobromuron, metolachlor, metoxuron, metribuzin, metsulfuron, monolinuron, norflurazon, orbencarb, axadiazon, oxyfluorfen, pendimethalin, proglinazine, propachlor, prosulfocarb, SMY 1500, sulfentrazone, terbutryn, fluthiamide (BAY FOE 5043), tri-allate, triasulfuron, trifluralin.

In the case of treatment of rice cultivations, the herbicidal compositions of the present invention comprise, in addition to the arylthiadiazolone having general formula (I), one or more of the following herbicides (b), to be selected from those listed above, on the basis of the method of use and weeds to be eliminated: acifluorfen, anilofos, azimsulfuron (DPX-A8947), bensulfuron, bensulide, benzofenap, bifenox, bispyribac-sodium (KHI-2023), bromobutide, butachlor, butenachlor, butralin, cafenstrole (CH-900), chlomethoxyfen, chlornitrofen, chlorpropham, cinmethylin, cinosulfuron, clomeprop, cumyluron, cyclosulfamuron (AC-322,140), daimuron, dichlobenil, diethatyl, dimepiperate, dimethametryn, esprocarb, ethoxysulfuron (HOE 095404), fluchloralin, halosulfuron (NC-319), mefenacet, methyldymron, molinate, naproanilide, oxadiargyl, oxadiazon, oxaziciclomefone (MY-100), pentoxazone, piperophos, pretilachlor, propanil, pyrazolinate, pyrazosulfuron, pyrazoxyfen, pyribenzoxim (LGC-40863), pyributicarb, pyriminobac-methyl (KIH-6127), quinclorac, simetryn, thenylchlor (NSK-850), thiobencarb, tiocarbazil.

For practical use in agriculture, it is often advantageous to use the herbicidal compositions of the present invention in the form of suitable formulations. This can be achieved either by formulating an arylthiadiazolone having general formula (I) with one or more herbicides (b) selected from those listed above, to give the desired composition, or forming the composition at the moment of use by mixing suitable quantities of an arylthiadiazolone having general formula (I) with one or more herbicides selected from those listed above, formulated separately.

Compositions can be used in the form of dry powders, wettable powders, emulsifiable concentrates, emulsions, microemulsions, suspoemulsions, gels, pastes, flakes, solutions, suspensions, pellets, tablets, films, etc.: the selection of the type of composition depends on the specific use.

The compositions are prepared according to the known methods, for example by diluting or dissolving the active substance(s) with a solvent medium and/or solid diluent, optionally in the presence of surface-active agents.

Liquid diluents which can be used, apart from water naturally, are various solvents such as, for example, N,N-dimethylformamide; dimethylsulfoxide; N-alkylpyrrolidones (N-methylpyrrolidone, etc.); aliphatic hydrocarbons (hexane, cyclohexane, etc.); aromatic hydrocarbons (xylols, mixtures of alkylbenzols, alkylnaphthalenes, etc.); chloroaromatics (chlorobenzol); alcohols (methanol, propanol, butanol, octanol, cyclohexanol, decanol, tetrahydrofurfurylic alcohol, etc.); glycols (ethylene glycol, propylene glycol, etc.); ketones (acetone, cyclohexanone, 2-heptanone, acetophenone, isophorone, 4-hydroxy-4-methyl-2-pentanone, etc.); esters (isobutyl acetate, etc.); vegetable or mineral oils; or their mixtures.

Solid inert diluents, or carriers, which can be used are kaolin, alumina, attapulgite, bentonite, kaolin, montmorillonite, calcite, dolomite, chalk, pumice, quartz, sand, silica, talc, seppiolite, diatomaceous earth, starch, cellulose, sugars, urea, calcium carbonate, sodium carbonate, sodium bicarbonate, sodium sulfate, etc.

Surface-active agents which can be used are emulsifying and wetting agents of the non-ionic type such as, for example, polyethoxylated aliphatic and cycloaliphatic alcohols, polyethoxylated alkyl-phenols, esters of fatty acids of polyethyoxylated sorbitan, hydrosoluble polyadducts of polyethylene oxides with polypropylene glycols, or with ethylene-diamino polypropylene glycols, or with alkyl-polypropylene glycols, etc; of the anionic type such as, for example, metal or ammonium salts of $C_{10}$–$C_{22}$ fatty acids, or of alkyl-aryl sulfonates, or of alkylsulfonates, or of alkylsulfates, sulfonate derivatives of benzimidazoles, etc; of the cationic type such as, for example, quaternary salts of $C_8$–$C_{22}$ alkylammonium, etc.

The above compositions can also contain dispersing agents (for example lignin and its salts, derivatives of cellulose, alginates, etc.), stabilizers (for example antioxidants, UV-ray absorbers, etc.), antifoam agents (for example, silicone oil, etc.), thickeners.

If desired, it is possible to add other compatible active principles to the herbicidal compositions of the present invention, such as, for example, other herbicides, fungicides, phytoregulators, antibiotics, insecticides, fertilizers.

The herbicidal compositions of the present invention usually contain from 0.1% to 99% by weight, preferably from 1% to 95% by weight, of a combination of an arylthiadiazolone having general formula (I) with one or more herbicides (b) selected from those listed above, from 1% to 99.9% by weight of a liquid or solid diluent and from 0% to 25% by weight, preferably from 0.1% to 20% by weight of a surface-active agent.

The following examples are purely illustrative and do not limit the scope of the present invention.

EXAMPLE 1

Preparation of 3-[2,4-Dichloro-5-(2-propinyloxy) phenyl]-5-(1,1-dimethylethyl)-1,3,4-thiadiazol-2 (3H)-one (Compound Nr. 1)

0.5 g (2.5 mmoles) of trichloromethylchloroformiate are added to a solution of 1.65 g (5 mmoles) of N'-[2,4-dichloro-5-(2-propinyloxy)phenyl]-N-thiopivaloyl-hydrazine in 25 ml of dioxane, maintained in a nitrogen atmosphere.

The mixture thus obtained is maintained under stirring, at room temperature, for 3 hours. The mixture is then poured into water (250 ml) and extracted with ethyl ether (3×10 ml). The organic phase obtained is washed until it becomes neutral, with a saturated solution of sodium chloride, anhydrified with sodium sulfate and concentrated by means of a rotavapor.

The raw product thus obtained is purified by silica gel chromatography eluating with n-hexane/ethyl acetate in a ratio of 9:1. 1.4 g of a solid product are obtained having a melting point of 92° C., corresponding to Compound Nr. 1.

EXAMPLE 2

Using the same procedure described in Example 1, the following compounds are prepared:

3-[4-chloro-2-fluoro-5-(2-propinyloxy)phenyl]-5-(1,1-dimethylethyl)-1,3,4-thiadiazol-2(3H)-one (Compound Nr. 2; m.p.: 73° C.–74° C.);

5-cyclopropyl-3-[2,4-dichloro-5-(2-propinyloxy)phenyl]-1,3,4-thiadiazol-2(3H)-one (Compound Nr. 3; m.p.: 99° C.–101° C.);

5-cyclopropyl-3-[4-chloro-2-fluoro-5-(2-propinyloxy) phenyl]-1,3,4-thiadiazol-2(3H)-one (Compound Nr. 4; dense oil);

3-[2,4-dichloro-5-(2-propinyloxy)phenyl]-5-(1-methylethyl)-13,4-thiadiazol-2(3H)-one (Compound Nr. 5; m.p.: 55° C.–57° C.);

3-[4-chloro-2-fluoro-5-(2-propinyloxy)phenyl]-5-(1-methylethyl)-1,3,4-thiadiazol-2(3H)-one (Compound Nr. 6; dense oil);

3-[2,4-dichloro-5-(2-propinyloxy)phenyl]-5-ethyl-1,3,4-thiadiazol-2(3H)-one (Compound Nr. 7; m.p.: 100° C.–101° C.)

3-[4-chloro-2-fluoro-5-(2-propinyloxy)phenyl]-5-ethyl-1,3,4-thiadiazol-2(3H)-one (Compound Nr. 8; m.p.: 93° C.–94° C.);

3-[2,4-dichloro-5-(2-propinyloxy)phenyl]-5-(1-methylcyclopropyl)-1,3,4-thiadiazol-2(3H)-one (Compound Nr. 9; m.p.: 117° C.–119° C.);

3-[4-chloro-2-fluoro-5-(2-propinyloxy)phenyl]-5-(1-methylcyclopropyl)-1,3,4-thiadiazol-2(3H)-one (Compound Nr. 10; m.p.: 95° C.–97° C.).

EXAMPLE 3

Determination of the Herbicidal Activity in Pre-emergence

The herbicidal activity and the phytotoxicity of the compositions of the present invention, in pre-emergence treatment, was evaluated according to the following operating procedures.

Pots (diameter 10 cm, height 10 cm) containing sandy earth were prepared. In each of them a weed or crop was sown.

The pots were divided into four groups, each containing 5 pots for each weed and crop.

Twenty-four hours after sowing, the pots were dampened with a light shower. An hour after watering, the first group of pots is treated with a hydroacetone dispersion containing the composition under evaluation, acetone (10% by volume) and Tween 20 (0.5%).

The second group of pots was treated with a hydroacetone dispersion containing the amount of arylthiadiazolone used in the composition, acetone (10% by volume) and Tween 20 (0.5%).

The third group of pots was treated with a hydroacetone dispersion containing the amount of known herbicide used in the composition, acetone (10% by volume) and Tween 20 (0.5%).

The fourth group of pots was treated with a hydroacetone solution containing acetone (10% by volume) and Tween 20 (0.5%), and was used as a comparison (control).

After the treatment, all the pots were uniformly watered every two days and kept in a conditioned environment under the following conditions:

temperature: 24° C.;

relative humidity: 60%;

photoperiod: 16 hours;

luminous intensity: 10000 lux.

Twenty-eight days after treatment, the herbicidal activity and the phytotoxicity of the composition was assessed in comparison with that of the single components and the control.

In the following Table 1 are reported, subdivided by crop, the composition of arylthiadiazolones of general formula I ($1^{st}$ component) with known herbicides ($2^{nd}$ component) for which improved herbicidal activity and/or reduced phytotoxicity with respect to the additive effect of the single components has been observed.

TABLE 1

| Crop | Compound Nr ($1^{st}$ component) | Known herbicide ($2^{nd}$ component) |
| --- | --- | --- |
| Maize | 1* | acetochlor; aclonifen; alachlor; ametryn; atrazine; BAY FOE 5043; benfuresate; bifenox; buthylate; clomazone; cyanazine; diethatyl ethyl; dimethenamid; EPTC; ethalfluralon; flumetsulam; halosulfuron methyl; indanofan; isoxaflutole linuron; methabenzthiazuron; metobromuron; metolachlor; metosulam monolinuron; orbencarb; oxyfluorfen; pendimethalin; propachlor; terbutilazine; triallate; vernolate |
| Wheat/barley | 1* | aclonifen; BAY FOE 5043, bifenox; cyclosulfamuron; chlorsulfuron; chlortoluron; diflufenican; ethoxysulfuron; fluoroglycofen; flupoxam flurtamone; indanofan; isopropazol; isoproturon; isoxaben; KPP 300; KPP 421; linuron; methabenzthiazuron; metoxuron; MON 375-00; monolinuron; neburon; orbencarb; oxyfluorfen; pendimethalin; prosulfocarb; siduron; triallate; trifluralin; UCC 4243; |

TABLE 1-continued

| Crop | Compound Nr (1st component) | Known herbicide (2nd component) |
|---|---|---|
| Rice | 1* | anilofos; fentrazamide (BAY YRC 2388); BAY FOE 5043; benfuresate; bifenox; cafenstrole; chlomethoxyfen; chlornitrofen; chlorpropham; cinmethylin; cyclosulfamuron; daimuron; dimepiperate; dimethametryn; esprocarb; ethabenzanid; ethoxysulfuron; fluoroglycofen; indanofan; mefenacet; molinate; oxadiargyl; oxadiazon; oxaziclomefone; pentoxazone; piperophos; pretilachlor; pyrazolinate; pyrazoxyfen; pyributicarb; pyrazosulfuron ethyl; quinclorac; simetryn; thiobencarb; tiocarbazil; |
| Soya bean | 1* | BAY FOE 5043; bifenox; chlorbromuron; chlorimuron; chlorpropham; chlorthal; clomazone; dimethenamid; ethalfluralin; flumetsulam; flumioxazin; fluoroglycofen; fomesafen; imazaquin; imazethapyr; indanofan; linuron; metolachlor; naptalam; norflurazon; orbencarb; oryzalin; oxyfluorfen; propachlor; sulfentrazone; thiazopyr; trifluralin; vernolate; |
| Cotton | 1* | chlorpropham; chlorthal; dimefuron; DPXT 5975; ethalfluralin; fluometuron; indanofan; linuron; metolachlor; norflurazon; orbencarb; oryzalin; oxyfluorfen; prometryn; propachlor; thiazopyr; |
| Sunflower | 1* | aclonifen; chlorbromuron; chlorpropham; ethalfluralin; flurochloridone; flurtainone; linuron; metolachlor; triallate; |
| Sugar-cane | 1* | acetochlor; bromacil; cyanazine; dimethametryn; ethoxysulfuron; fluometuron; isoxaflutole; linuron; metolachlor; oxadiargyl; propachlor; sulfentrazone tebuthiuron; therbacil; thiazopyr. |

*Compound described in Example 1.

What is claimed is:
1. A herbicidal composition, comprising:
(a) at least one arylthiadiazole having the formula (I):

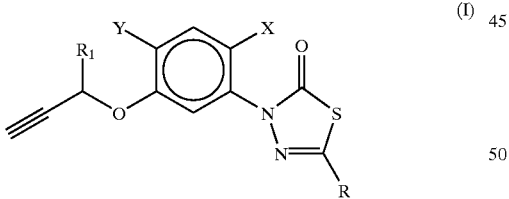

wherein:
R represents linear or branched $C_1$–$C_6$ alkyl or haloalkyl; or $C_3$–$C_5$ cycloalkyl or halocycloalkyl; said alkyl, haloalkyl, cycloalkyl or halocycloalkyl being optionally substituted with linear or branched $C_1$–$C_3$ alkyl;
X represents halogen;
Y represents halogen; linear or branched $C_1$–$C_4$ alkyl or haloalkyl; linear or branched $C_1$–$C_4$ alkoxyl or haloalkoxyl;
$R_1$ represents hydrogen or methyl; and
(b) one or more herbicidal compounds selected from the group consisting of chloramben, chlorthal, dicamba, naptalam, 2,3,6-TBA, clopyralid, diflufenzopyr (SAN 835 H), dithiopyr, picloran, thiazopyr (MON 13200), quinclorac, quinmerac, indanofan (MK-243), benazolin, chlorflurenol, dalapon, endothal, flamprop, flamprop M, flupropanate, flurenol, TCA-sodium, bromobutide, chlorthiamid, diflufenican, diphenamid, ethabenzanid (HW 52), isoxaben, mefenacet, monalide, pentanochlor, propanil, propyzanide, tebutam, fluthiamide (BAY FOE 5043), clodinafop, clomeprop, cyhalofop-butyl (XDE-537), 2,4-D, 2,4-DB, dichlorprop, dichlorprop-P, diclofop, fenoxaprop, fenoxaprop-P, fluazifop, fluazifop-P, fluroxypyr, haloxyfop, haloxyfop-P-methyl, isoxapyrifop, MCPA, MCPA-thioethyl, MCPB, mecoprop, mecoprop-P, naproanilide, napropamide, propaquiazfop, quizalofop, quizalofop-P, triclopyr, UBI-C474, bromofenoxim, bromoxynil, dichlobenil, ioxynil, diquat, paraquat, asulam, butylate, carbetamide, chlorbufam, chlorpropham, cycloate, desmedipham, dimepiperate, EPTC, esprocarb, molinate, orbencarb, pebulate, phenmedipham, propham, prosulfocarb, pyributicarb, thiobencarb, tiocarbazil, tri-allate, vernolate, alloxydim, butroxydim, clethodim, cylcoxydim, sethoxydim, sulcotrione, tralkoxydim, acetochlor, alachlor, butachlor, butenachlor, diethatyl, dimethachlor, dimethenamid, metazochlor, metolachlor, pretilachlor, propachlor, propisochlor, tenylchlor (NSK-850), acifluorfen, aclonifen, bifenox, chlomethoxyfen, chlornitrofen, athoxyfenethyl (RC-252), fluoroglycofen, fluoronitrofen, fomesafen, furyloxyfen, lactofen, AKH-7088, oxyfluorfen, benfluralin, butralin, dinitramide, ethalfluralin, fluchloralin, isopropalin, oryzalin, pendimethalin, prodiamine, trifluralin, dinoseb, dinoseb acetate, dinoterb, amitrole, benfuresate, bentazone, benzofenap, cafenstrole (CH-900), carfentrazone-ethyl (F-8426), chloridazon, cinmethylin, clomazone, difenzoquat, ethofumesate, pyraflufen-ethyl (ET-751), flumichloracpentyl, flumioxazin, flumipropin, flupoxam, fluridone, flurochloridone, flurtamone, fluthiacet methyl (KIH-9201), isoxaflutone (RPA 201772), methazole, nipyraclofen, norflurazon, oxadiargyl, oxadiazon, oxaziclomefone (MY-100), pentoxazone (KPP-3 14), pyruzolynate, pyrazoxyfen, pyridate, sulfentrazone, (F6285), thidiazimin, anilofos, bensulide, bilanafos, butamifos, fosamine, glufosinate, glyphosate, LS830556, piperophos, imazamethabenz, imazamethipyr (AC-263,222), imazamox (AC-299,263), imazapyr, imazaquin imazethapyr, bispyribac-sodium (KHI-2023), pyribenzoxim (LGC-40863), pyriminobac-methyl (KIH-6127), pyrithiobac-sodium (KIH-2031), tioclorim, cloransulam-methyl (XDE-565), diclosulam (XDE-564), flumetsulam (DE-498), metosulam (XDE-564), flumetsulam (DE-498), metosulam (DE-511), amidosulfuron, azimsulfuron (DPX-A8947), bensulfuron, chlorimuron, chlorsulfuron, cinosulfuron, cyclosulfamuron (AC-322,140), ethametsulfuron-methyl (DPX-A7881), ethoxysulfuron (HOE 095404), flazasulfuron, flupyrsulfuron (DPX-KE459), halosulfuron (NC-319), imazosulfuron, metsulfuron, NC-300, nicosulfuron, oxasulfuron (CGA-277476), primisulfuron, prosulfuron (CGA-152005), pyrazolsulfuron, rimsulfuron, sulfometuron (DPX-5648), sulfosulfuron (MON-37500), thifensulfuron, triasulfuron (CGA-121036), tribenuron, triflusulfuron-methyl (DPX-66037), ametryn, atrasin, aziprotryne, cyanazine, desmetryn, dimethame-tryn, dipropetryn, eglinazine, methoprotryne, proglinazine, prometon, prometryne, propazine, simazine, simetryn, terbumeton, terbuthylazine, terbutryn, triaziflam (IDH-1105), trietazine, SMY-1500, hexazinone, metamitron, metribuzin, bromacil, lenacil, terbacil, benzthiazuron, chlorbromuron, chloroxuron, chlorotoluron, cumyluron (JC-940), daimuron, difenoxuron, dimefuron, 1-diuron, ethidimuron, fenuron, fluometuron, isoproturon, isouron, linuron, methabenzthiazuron, methyldymron, metobenzuron, metobromuron, metoxuron, monolinuron, neburon, siduron, tebuthiuron, thiazafluoron, isopropazol (JV 485), KPP 300, KPP 421, BAY YRL 2388, DPXT 5975, azafenidin.

2. The herbicidal composition of claim 1, wherein the one or more arylthiadiazolones having the formula (I) are:

3-[2,4-dichloro-5-(2-propinyloxy)phenyl]-5-(1,1-dimethylethyl)-1,3,4-thiadiazole-2(3H)-one;

3-[4-chloro-2-fluoro-5-(2-propinyloxy)phenyl]-5-(1,1-dimethylethyl)-1,3,4-thiadiazole-2(3H)-one;

5-cyclopropyl-3-[2,4-dichloro-5-(2-propinyloxy)phenyl]-1,3,4-thiadiazol-2(3H)-one;

5-cyclopropyl-3-[4-chloro-2-fluoro-5-(2-propinyloxy)penyl]-1,3,4-thiadiazole-2(3H)-one;

3-[2,4-dichloro-5-(2-propinyloxy)phenyl]-5-(1-methylethyl)-1,3,4-thiadiazole-2(3H)-one;

3-[4-chloro-2-fluoro-5-(2-propinyloxy)phenyl]-5-(1-methylethyl-1,3,4-thiadiazole-2(3H)-one;

3-[2,4-dichlor-5-(2-propinyloxy)phenyl]-5-ethyl-1,3,4-thiadiazol-3(3H)-one;

3-[4-chloro-2-fluoro-5-(2-propinyloxy)phenyl]-5-ethyl-1,3,4-thiadiazol-2(3H)-one;

3-[2,4-dichloro-5-(2-propinyloxy)phenyl]-5-(1-methylcyclopropyl)-1,3,4thiadiazol-2(3H)-one;

3-[4-chloro-2-fluoro-5-(2-propinyloxy)phenyl]-5-(1-methylcyclopropyl)-1,3,4-thiadiazole-2(3H)-one;

(±)-3-[2,4-dichlorophenyl-5-(1-methyl-2-propinyloxy)phenyl]-5-(1,1-dimethylethyl)-1,3,4-thiadiazol-2(3H)-one;

(±)-3-[4-chloro-2-fluoro-5-(1-methyl-2-propinyloxy)phenyl]-5-(1,1-dimethylethyl)-1,3,4-thiadiazol-2(3H)-one;

(±)-5-cyclopropyl-3-[2,4-dichloro-5-(1-methyl-2-propinyloxy)phenyl]-1,3,4-thiadiazol-2(3H)-one;

(±)-5-cyclopropyl-3-[4-chloro-2-fluoro-5-(1-methyl-2-propinyloxy)phenyl]1,3,4-thiadiazole-2(3H)-one;

(±)-3-[2,4-dichloro-5-(1-methyl-2-propinyloxy)phenyl]-5-(1-methylethyl)-1,3,4-thiadiazol-2(3H)-one;

(±)-3-[4-chloro-2-fluoro-5-(1-methyl-2-propinyloxy)phenyl]-5-(1-methylethyl)-1,3,4-thiadiazole-2(3H)-one;

(±)-3-[2,4-dichloro-5-(1-methyl-2-propinyloxy)phenyl]-5-ethyl-1,3,4-thiadiazol-2(3H)-one;

(±)-3-[4-chloro-2-fluoro-5-(1-methyl-2-propinyloxy)phenyl]-5-ethyl-1,3,4-thiadiazol-2(3H)-one;

(±)-3-[2,4-dichloro-5-(1-methyl-2-propinyloxy)phenyl]-5-(1-methylcyclopropyl)-1,3,4-thiadiazole-2(3H)-one; or (±)-3-[4-chloro-2-fluoro-5-(1-methyl-2-propinyloxy)phenyl]-5-(1-methylcyclopropyl)-1,3,4-thiadiazol-2(3H)-one.

3. The herbicidal composition of claim 1, wherein a ratio between the weight quantity of the arylthiadiazolone having the formula (I) and a weight quantity of the product(s) with the herbicidal activity (b), varies from 99.9:0.1 to 0.1:99.9.

4. The herbicidal composition of claim 3, wherein a ratio between the weight quantity of the arylthiadiazolone having the formula (I) and a weight quantity of the product( ) with a herbicidal activity (b), varies from 99:1 to 1:99.

5. The herbicidal composition of claim 1, wherein the herbicides (b) are selected from the group consisting of acetochlor, acifluorfen, aclonifen, alachlor, ametryn, atrazine, bifenox, butralin, chloramben, clomazone, chlorbromuron, chlorotoluron, chlorsulfuron, cyanazine, cyclosulfamuron (AC-322,140), diethatyl, diflufenican, dimethenamid, diphenamid, eglinazine, fluchloralin, flumioxazin, fluoroglycofen, flupoxam, flurochloridone, flurtamone, halosulfuron (NC-319), imazaquin, imazethapyr, isoproturon, isoxaben, isoxaflutole (RPA 201772), linuron, metazachlor, metoxuron, metribuzin, metsulfuron, monolinuron, norflurazon, orbencarb, axadiazon, oxyfluorfen, pendimethalin, proglinazine, propachlor, prosulfocarb, SMY 1500, sulfentrazone, terbutryn, fluthiamide (BAY FOE 5043), triallate, triasulfuron, trifluralin.

6. The herbicidal composition of claim 1, wherein the herbicides (b) are selected from the group consisting of acifluorfen, anilofos, azimsulfuron (DPX-A8947), bensulfuron, bensulide, benzofenap, bifenox, bispyribac-sodium (KHI-2023), bromobutide, butachlor, butenachlor, butralin, cafenstrole (CH-900), chlomethoxyfen, chlornitrofen, chlorpropham, cinmethylin, cinosulfuron, clomeprop, cumyluron, cyclosulfamuron (AC-322,140), daimuron, dichlobenil, diethatyl, dimepiperate, dimethametryn, esprocarb, ethoxysulfuron (HOE 095404), fluchloralin, halosulfuron (NC-319), mefenacet, methyldymron, molinate, naproanilide, oxadiargyl, oxadiazon, oxaziciclomefone (MY-100), pentoxazone, piperophos, pretilachlor, propanil, pyrazolinate, pyrazolsulfuron, pyrazoxyfen, pyribenzoxim (LGC-40863), pyributicarb, pyriminobac-methyl (KIH-5127), quinclorac, simetryn, thenylchlor (NSK-850), thiobencarb, tiocarbazil.

7. The herbicidal composition of claim 1, further comprising liquid diluents, solid diluents, surface-active agents, dispersing agents, stabilizers, antifoam agents, thickeners.

8. The herbicidal composition of claim 1, which further comprises other herbicides, fungicides, phytoregulators, antibiotics, insecticides, fertilizers, are present.

9. The herbicidal composition of claim 1, which contains from 0.1% to 99% by weight of a combination of an arylthiadiazolone having the formula (I) with one or more herbicides (b) selected from those listed above, from 1% to 99.9% by weight of a liquid or solid diluent and from 0% to 25% by weight of a surface-active agent.

10. A method of controlling weed growth amidst agricultural crops, which comprises administering an effective amount of the herbicidal composition of claim 1, to the weeds.

11. The method of claim 10, wherein said effective amount comprises between 1 g/ha and 5 kg/ha of the arylthiadiazolone having the formula (I).

12. The method of claim 11, wherein said effective amount comprises between 10 g/ha and 500 g/ha of the arylthiadiazolone having the formula (I).

* * * * *